(12) United States Patent
Akiyama et al.

(10) Patent No.: US 9,134,265 B2
(45) Date of Patent: Sep. 15, 2015

(54) GAS SENSITIVE MATERIAL COMPRISING MICROCRYSTALLINE SELENIUM AND GAS SENSOR USING SAME

(75) Inventors: Norio Akiyama, Okayama (JP); Tsukio Ohtani, Okayama (JP)

(73) Assignee: Kake Educational Institution, Okayama (JP)

( * ) Notice: Subject to any disclaimer, the term of this patent is extended or adjusted under 35 U.S.C. 154(b) by 495 days.

(21) Appl. No.: 13/508,292

(22) PCT Filed: Nov. 4, 2010

(86) PCT No.: PCT/JP2010/069614
§ 371 (c)(1),
(2), (4) Date: Jul. 9, 2012

(87) PCT Pub. No.: WO2011/055751
PCT Pub. Date: May 12, 2011

(65) Prior Publication Data
US 2012/0266658 A1    Oct. 25, 2012

(30) Foreign Application Priority Data
Nov. 5, 2009  (JP) ................................ 2009-254461

(51) Int. Cl.
*G01N 27/12*  (2006.01)

(52) U.S. Cl.
CPC ............ *G01N 27/125* (2013.01); *G01N 27/127* (2013.01)

(58) Field of Classification Search
CPC ........................... G01N 27/125; G01N 27/127

USPC .............................................. 73/31.05, 31.06
See application file for complete search history.

(56) References Cited

U.S. PATENT DOCUMENTS

| | | | |
|---|---|---|---|
| 3,622,712 A * | 11/1971 | Moore et al. ................... | 369/137 |
| 4,287,279 A * | 9/1981 | Brown et al. ................. | 430/57.8 |
| 5,618,496 A | 4/1997 | Hasumi et al. | |
| 8,101,061 B2 * | 1/2012 | Suh et al. ....................... | 205/688 |
| 2006/0076504 A1* | 4/2006 | de Jonge et al. ........... | 250/423 F |

(Continued)

FOREIGN PATENT DOCUMENTS

| | | |
|---|---|---|
| EP | 1 816 240 A1 | 8/2007 |
| JP | 31-004900 B1 | 6/1956 |

(Continued)

OTHER PUBLICATIONS

Candeloro et al., *J. Vac. Sci. Technol. B*, 23(6): 2784-2788 (2005).
(Continued)

*Primary Examiner* — Peter Macchiarolo
*Assistant Examiner* — Nathaniel Kolb
(74) *Attorney, Agent, or Firm* — Leydig, Voit & Mayer, Ltd.

(57) ABSTRACT

The invention provides a gas sensitive material made from microcrystalline selenium (preferably selenium nanowire) and a gas sensor having an element structure wherein the gas sensitive material is disposed between two electrodes.

The invention allows for the kind of organic gas to be distinguished, because microcrystalline selenium reacts with organic gas molecules with high sensitivity at room temperature without being influenced by humidity, and the magnitude of change of the value of the current flowing at a fixed voltage varies depending on the kind of an organic gas to be sensed.

17 Claims, 14 Drawing Sheets

(56) References Cited

U.S. PATENT DOCUMENTS

2006/0284218 A1* 12/2006 Kaner et al. ............. 257/288
2007/0170071 A1*  7/2007 Suh et al. ................ 205/687
2008/0211040 A1*  9/2008 Lieber et al. ............. 257/414

FOREIGN PATENT DOCUMENTS

| | | |
|---|---|---|
| JP | 50-010756 B1 | 4/1975 |
| JP | 54-006913 B2 | 4/1979 |
| JP | 3081244 B2 | 6/2000 |
| JP | 2004-515782 A | 5/2004 |
| JP | 2005-214868 A | 8/2005 |
| JP | 4205601 B2 | 10/2008 |
| JP | 2009-098121 A | 5/2009 |
| WO | WO 02/48701 A2 | 6/2002 |

OTHER PUBLICATIONS

Karthigeyan et al., *Japanese Journal of Applied Physics*, 47(9): 7440-7443 (2008).
Ohtani et al., *Chemistry Letters*, 33(2): 100-101 (2004).
Japanese Patent Office, International Search Report in International Patent Application No. PCT/JP2010/069614 (Nov. 30, 2010).
International Bureau of WIPO, International Preliminary Report on Patentability in International Patent Application No. PCT/JP2010/069614 (Sep. 9, 2011).

* cited by examiner (a)

(b)

(c)

(a)

(b)

(c)

acetone                    benzene (a)

(b)

(c)

(d)

D=565 nm

D=274 nm

D=233 nm

GAS SENSITIVE MATERIAL COMPRISING MICROCRYSTALLINE SELENIUM AND GAS SENSOR USING SAME

CROSS-REFERENCE TO RELATED APPLICATIONS

This patent application is a U.S. National Phase of PCT/JP2010/069614, filed Nov. 4, 2010, which claims the benefit of Japanese Patent Application No. 2009-254461, filed Nov. 5, 2009, which is incorporated by reference.

TECHNICAL FIELD

The present invention relates to a gas sensitive material comprising microcrystalline selenium and a novel gas detection technique comprising detecting a gas (particularly organic gas) by using the gas sensitive material.

BACKGROUND ART

In recent years, detection of gas in the environment has become increasingly important for avoidance of danger caused by noxious gas, odorless carbon monoxide gas and the like in the environment. As a gas sensor for detection of such gas in the environment, semiconductor type gas sensors are conventionally known (e.g., patent document 1). This gas sensor is a P-N type gas sensor that electrically detects resistance value that changes when N-type semiconductor and P-type semiconductor made from metal oxide and in contact with each other are maintained at a high temperature and a gas in the environment comes into contact with the contact part of the both semiconductors, where the detection utilizes change of resistance value of the sensor. Recently, a P-N type carbon monoxide gas sensor capable of detecting carbon monoxide gas with high selectivity has also been proposed (patent document 2). In recent times, considerations have been made of a gas sensor using a single-walled carbon nanotube (SWCNT) (non-patent document 1, patent document 3), and a gas sensor using a stannous oxide ($SnO_2$) nanowire (non-patent document 2).

P-N type gas sensors can simultaneously detect, besides carbon monoxide gas, organic gases such as methane, ethanol, ethyl acetate and the like. In addition, P-N type carbon monoxide gas sensor can detect carbon monoxide gas alone. However, when used singly, such gas sensors cannot distinguish the kind of gas with good sensitivity. It lacks stability at room temperature, requires detection at a high temperature using a heater, and consumes a large amount of electric power. Moreover, since bulk crystal is used for a metal oxide semiconductor, sufficient detection sensitivity can be obtained only when a gas detector part (laminate of N-type semiconductor device and P-type semiconductor device) has a certain large size, which prevents sufficient downsizing of the sensor. On the other hand, when a gas detector part has a large size to improve sensitivity, gas detection responsiveness becomes low. Since it requires a P-type semiconductor and an N-type semiconductor, the cost becomes high and the production steps become complicated.

A gas sensor using a single-walled carbon nanotube (SWCNT) contains the single-walled carbon nanotube (SWCNT) as a principal member, and production thereof requires a large-scale, complicated manufacturing equipment, thus posing problems in terms of cost and mass productivity. In addition, the gas to be the detection target is inorganic gas such as hydrogen gas, helium gas, argon gas and the like, dioxide nitrogen and the like, and the sensor is unsuitable for the detection and distinction of organic gas. Also, a gas sensor using a tin oxide ($SnO_2$) nanowire has a high operation temperature and requires heating, which leads to a high consumption power.

In recent years, building materials containing many noxious volatile organic compounds (formaldehyde, acetaldehyde, toluene, trichloroethylene, tetrachloroethylene, benzene, xylene, acetone, methanol and the like) such as paint, adhesive, waterproof material and the like are used in construction sites such as new construction of office building, apartment building and the like, repair work of outer wall etc., and the like. Emission of volatile organic compounds from such building materials into the surrounding environment has been recognized as one of the factors causing sick-house syndrome, and therefore, improvement of the detection technique of organic gas in the environment is important. Moreover, since such volatile organic compounds release explosive organic gas, improvement of the detection technique for avoidance of danger is important. Furthermore, the significance of an ethyl alcohol detection technique as a countermeasure against drunken driving is also increasing.

DOCUMENT LIST

Patent Documents patent document 1: JP-B-3081244
patent document 2: JP-B-4205601
patent document 3: JP-A-2009-98121
patent document 4: National Publication of International Patent Application No. 2004-515782

Non-Patent Documents non-patent document 1: A. Karthigeyan, N. Minami, and K. Iakoubovskii, Jpn. J. Appl. Phys. 47(2008) pp.7440-7443
non-patent document 2: P. Carpentiero et al. J. Vac. Sci. Technol B 23 (2005) pp. 2784

SUMMARY OF THE INVENTION

Problems to be Solved by the Invention

Therefore, the problem to be solved by the present invention is provision of an economical and compact gas sensor capable of detecting an organic gas with high sensitivity, which operates at room temperature, and a gas sensitive material therefor.

In addition, it is provision of an economical and compact gas sensor capable of distinguishing the kind of an organic gas, which operates at room temperature, and a gas sensitive material therefor.

Means of Solving the Problems

The present inventors have conducted intensive studies in an attempt to solve the aforementioned problems and learned that an electric current flows when microcrystalline selenium resulting from crystal growth of amorphous selenium by a catalytic action of an organic solvent is placed at a fixed voltage, the current value thereof changes upon contact with an organic gas molecule at room temperature, and particularly, a selenium nanowire, which is fibrous or needle-shaped hexagonal microcrystalline selenium, has properties of a P-type semiconductor intrinsic to selenium and high sensitivity to organic gas molecule, and found that an organic gas can be detected by observing the changes of the value of the electric current flow through microcrystalline selenium under a fixed voltage at room temperature, the behavior of the current value change varies depending on the kind of the organic gas, and also, the kind of the organic gas can be distinguished, which resulted in the completion of the present invention.

Accordingly, the present invention relates to (1) a gas sensitive material comprising microcrystalline selenium,
(2) the gas sensitive material of the above-mentioned (1), wherein the microcrystalline selenium is a selenium nanowire,
(3) the gas sensitive material of the above-mentioned (1) or (2), which is for detection of an organic gas,
(4) the gas sensitive material of the above-mentioned (3), wherein the organic gas is a gas derived from a volatile organic compound having a relative permittivity of 1.0-38.0 at room temperature,
(5) a gas sensor having a device structure wherein the gas sensitive material of the above-mentioned (1) is disposed between two electrodes,
(6) a gas sensor having a device structure wherein the gas sensitive material of the above-mentioned (2) is disposed between two electrodes,
(7) the gas sensor of the above-mentioned (5) or (6), which is for detection of an organic gas,
(8) the gas sensor of the above-mentioned (7), wherein the organic gas is a gas derived from a volatile organic compound having a relative permittivity of 1.0-38.0 at room temperature,
(9) the gas sensor of any of the above-mentioned (5) to (8), which identifies gaseous species from a difference in the magnitude of change in a value of an electric current flowing between two electrodes at a fixed voltage,
(10) the gas sensor of any of the above-mentioned (5) to (8), which identifies, at a saturation sensitivity, gaseous species from a difference in the magnitude of change in a value of an electric current flowing between two electrodes, and
(11) the gas sensor of any of the above-mentioned (5) to (8), which identifies gaseous species from the difference in the temporal characteristic of the magnitude of change of a value of an electric current flowing between two electrodes at a fixed voltage, using difference in a relaxation time as an index.

Patent document 4 describes a nanowire sensor using a semiconductor nanowire and, as for the semiconductor nanowire, it is described by citing various known vapor growth methods as examples that nanosized microcrystalline selenium (selenium nanowire) is also produced by a vapor growth method in the same manner as with a silicon nanowire. However, nanosized microcrystalline selenium is not obtained by a vapor growth method, and an example of actual production of a selenium nanowire is not described. While a gas sensor is described, utilization of selenium for the detection or identification of an organic gas is not described at all.

Effect of the Invention

The gas sensitive material of the present invention, which is made from microcrystalline selenium, is easy to produce and economical, and therefore, provides high cost advantage as compared to gas sensitive materials used for conventional gas sensors. In addition, microcrystalline selenium reacts highly sensitively with an organic gas molecule at room temperature, and shows different magnitude of current value change at a fixed voltage, depending on the kind of the organic gas to be sensed. Therefore, the kind of the organic gas can be distinguished based on the difference in the magnitude of change.

The gas sensor of the present invention may have a simple sensor element structure wherein a gas sensitive material made from microcrystalline selenium is disposed between two electrodes and the amount of microcrystalline selenium to be disposed between the two electrodes can be small, and therefore, it can realize an economical, compact gas sensor which has an ability to distinguish an organic gas, and operates at room temperature. Particularly, since a selenium nanowire, which is a hexagonal microcrystalline selenium, is highly sensitive, and the amount thereof to be disposed between two electrodes can be very small, a compact gas sensor can be realized at a lower cost. In addition, since a heating means is not necessary, the energy cost is low. Moreover, a selenium nanowire, which is hexagonal microcrystalline selenium, can be regenerated to the original state by contact with an organic solvent after acting as a sensor device for a given period, semipermanent use thereof is also expected.

DESCRIPTION OF EMBODIMENTS

The present invention is explained in the following by referring to preferable embodiments.

The microcrystalline selenium in the present invention is produced by contacting amorphous selenium with an organic solvent at room temperature at least for several minutes to allow crystal growth (self-growth) from amorphous selenium, and includes hexagonal microcrystalline selenium (selenium nanowire) and monoclinic microcrystalline selenium.

Here, amorphous selenium is generally used by grinding to a fine powder having a particle size of about 20-30 μm. As an organic solvent to be contacted with amorphous selenium, a solvent having a relative permittivity (room temperature) of higher than 4.0, for example, acetone, pyridine, 2-propanol, acetonitrile, diethyl ether, benzylamine, piperidine, aniline, quinoline, acetophenone, benzonitrile and the like, and a solvent having a relative permittivity (room temperature) of lower than 4.0, for example, benzene, toluene, cyclohexane, hexane and the like are used.

When an organic solvent having a relative permittivity (room temperature) of higher than 4.0 is used as an organic solvent, a selenium nanowire having a nano size (generally several nm-800 nm), which is fibrous or needle-shaped hexagonal microcrystalline selenium having a length of about 1-10 μm, is produced. When an organic solvent having a relative permittivity (room temperature) of lower than 4.0 is used, microcrystalline selenium comprised of granular monoclinic polyhedron having a particle size of about 1-10 μm is produced. Microcrystalline (hexagonal system) selenium grown in a moderate curve is called "fibrous", microcrystalline (hexagonal system) selenium grown linear and rather short is called "needle-shaped", and the "selenium nanowire" is a concept including either of both of these. The "room temperature" in the present specification generally means the range of 20-25° C.

Figure 1:
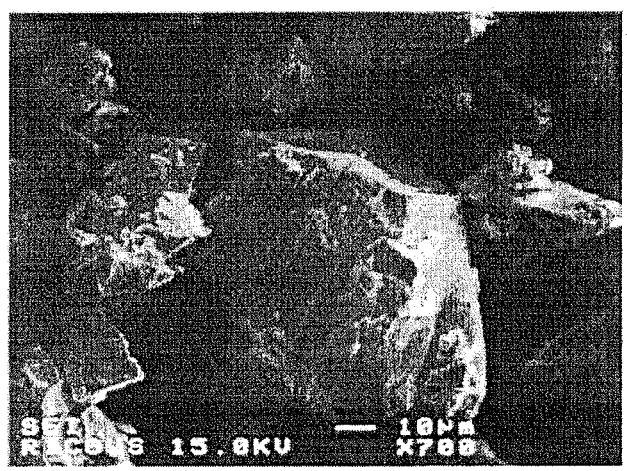
FIG. 1 shows (a) scanning electron microscope (SEM) photograph of amorphous selenium, (b) SEM photograph of nano-sized fibrous microcrystalline selenium (hexagonal system) and (c) SEM photograph of granular microcrystalline selenium (monoclinic system).
Figure 1:
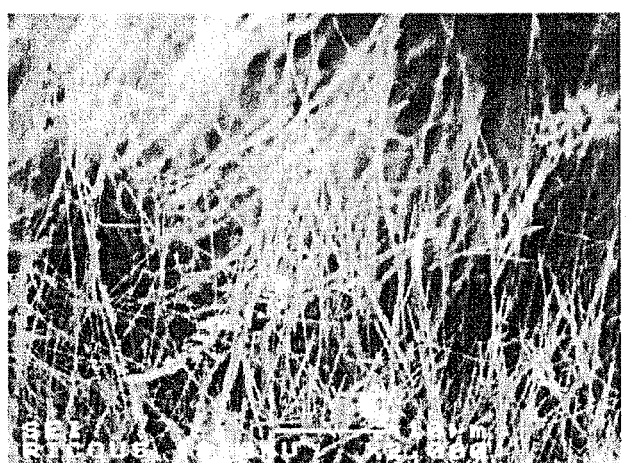
Figure 1:
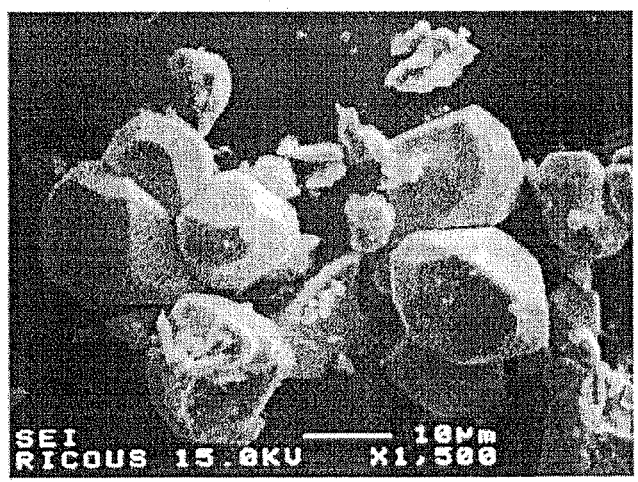

FIG. 1(a) is an SEM photograph of amorphous selenium, FIG. 1(b) is an SEM photograph of nano-sized fibrous microcrystalline selenium produced by contacting amorphous selenium with acetone for 10 days, and FIG. 1(c) is an SEM photograph of granular microcrystalline selenium produced by contacting amorphous selenium with benzene for 10 days.

Figure 2:
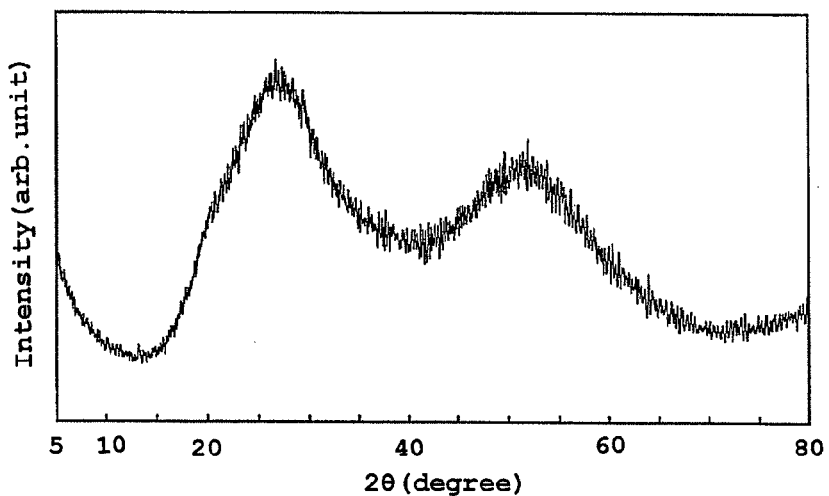
FIG. 2 shows (a) X-ray diffraction pattern of amorphous selenium, (b) X-ray diffraction pattern of nano-sized fibrous microcrystalline selenium (hexagonal system) and (c) X-ray diffraction pattern of granular microcrystalline selenium (monoclinic system).
Figure 2:
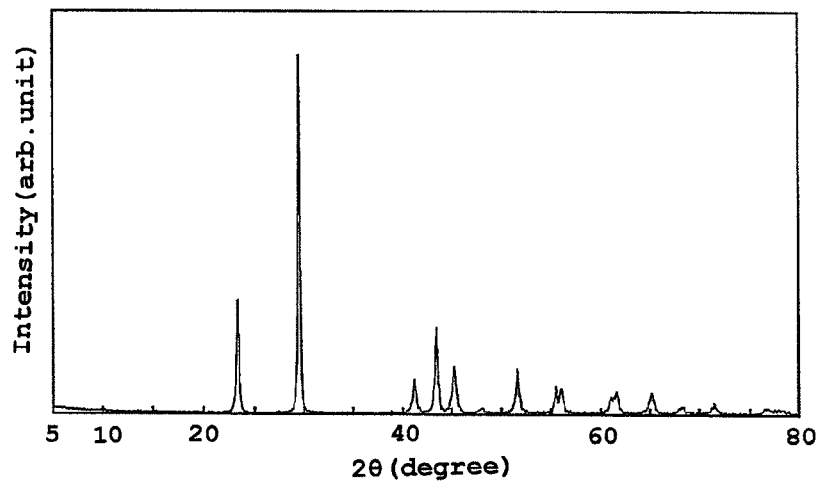
Figure 2:
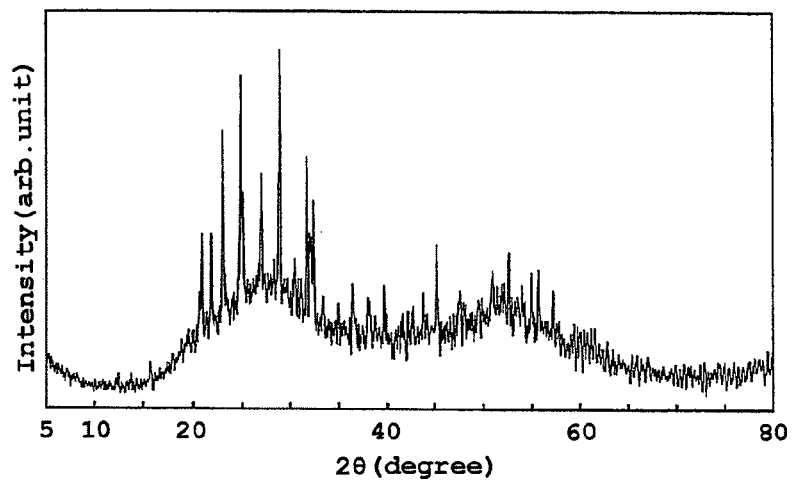

FIG. 2(a) is an X-ray diffraction pattern of the above-mentioned amorphous selenium, FIG. 2(b) is an X-ray diffraction pattern of fibrous microcrystalline selenium produced by contacting the above-mentioned amorphous selenium with acetone for 10 days, and FIG. 2(c) is an X-ray diffraction pattern of granular microcrystalline selenium produced by contacting the above-mentioned amorphous selenium with benzene for 10 days.

The diffraction pattern of FIG. 2(b) shows a hexagonal system, and the diffraction pattern of FIG. 2(c) shows a monoclinic system. In the diffraction pattern of FIG. 2(c), overlapping of the X-ray diffraction pattern due to the amorphous selenium of FIG. 2(a) is seen.

Amorphous selenium can be contacted with an organic solvent by an embodiment of placing amorphous selenium in the liquid of an organic solvent, an embodiment of placing amorphous selenium in vapor (gas) of an organic solvent, an embodiment of placing amorphous selenium in vapor (gas) of a solid organic substance and the like, which can be appropriately selected according to the form and the like of microcrystalline selenium to be produced. Even when monoclinic selenium is used instead of amorphous selenium, microcrystalline selenium can be produced in a similar manner.

The fibrous or needle-shaped hexagonal microcrystalline selenium (hereinafter to be also simply referred to as "selenium nanowire") has the intrinsic properties of a P-type semiconductor, is extremely stable (that is, a stable crystal form), and maintains the nano-sized fibrous or needle-shaped form even at high temperatures and low temperatures.

The shape and size of a selenium nanowire (thickness, length), and particle size and the like of microcrystalline selenium consisting of granular monoclinic polyhedron can be controlled by the kind of an organic solvent to be contacted with amorphous selenium, a method of contacting with an organic solvent, work environments (temperature, pressure) and the like.

The thickness of a selenium nanowire tends to grow as the relative permittivity of the organic solvent to be contacted with amorphous selenium is smaller and the contact time is longer, and tends to be thinner as the relative permittivity of the organic solvent to be contacted with amorphous selenium is higher and the contact time is shorter. In addition, the length of a selenium nanowire tends to be longer as the contact time with an organic solvent becomes longer, and shorter as the contact time with an organic solvent becomes shorter.

Even when the same solvent is used, the shape of a selenium nanowire to be formed changes depending on the manner of contact between amorphous selenium and the solvent. For example, as shown in the below-mentioned Table 1, a selenium nanowire formed by placing amorphous selenium in a vapor (gas) of acetone is thicker and shorter as compared to a selenium nanowire formed by placing amorphous selenium in the liquid of acetone.

When microcrystalline selenium is placed at a fixed voltage at room temperature, a certain amount of electric current flows through a selenium nanowire due to the electric conductivity mechanism based on the intrinsic properties of selenium as a P-type semiconductor. In addition, monoclinic microcrystalline selenium itself is an insulator, but a certain amount of electric current flows, though the current value is smaller than that of a selenium nanowire, presumably because of smaller grain diameter and surface conductivity due to a dirty surface. When microcrystalline selenium contacts an organic gas molecule at room temperature, it reacts with the organic gas molecule to increase its impedence. As a result, the current value decreases. When the organic gas is removed, the current value increases and microcrystalline selenium is restored to the state before contact with the organic gas. On the other hand, microcrystalline selenium can detect an organic gas by observing change in the value of a current flowing through the microcrystalline selenium at a fixed voltage. In particular, selenium nanowire shows extremely high reaction sensitivity with an organic gas molecule, and fast response rates of decrease and increase (restoration) of the electric current value. In addition, since the behavior of change in the value of current flowing in the microcrystalline selenium at a fixed voltage varies depending on the kind of an organic gas, the kind of an organic gas can be distinguished from, for example, difference in the magnitude of current value change at a fixed voltage. Microcrystalline selenium (particularly selenium nanowire) is stable in water, is not easily influenced by humidity, and can sense (detect) an organic gas with high sensitivity.

Figure 3:
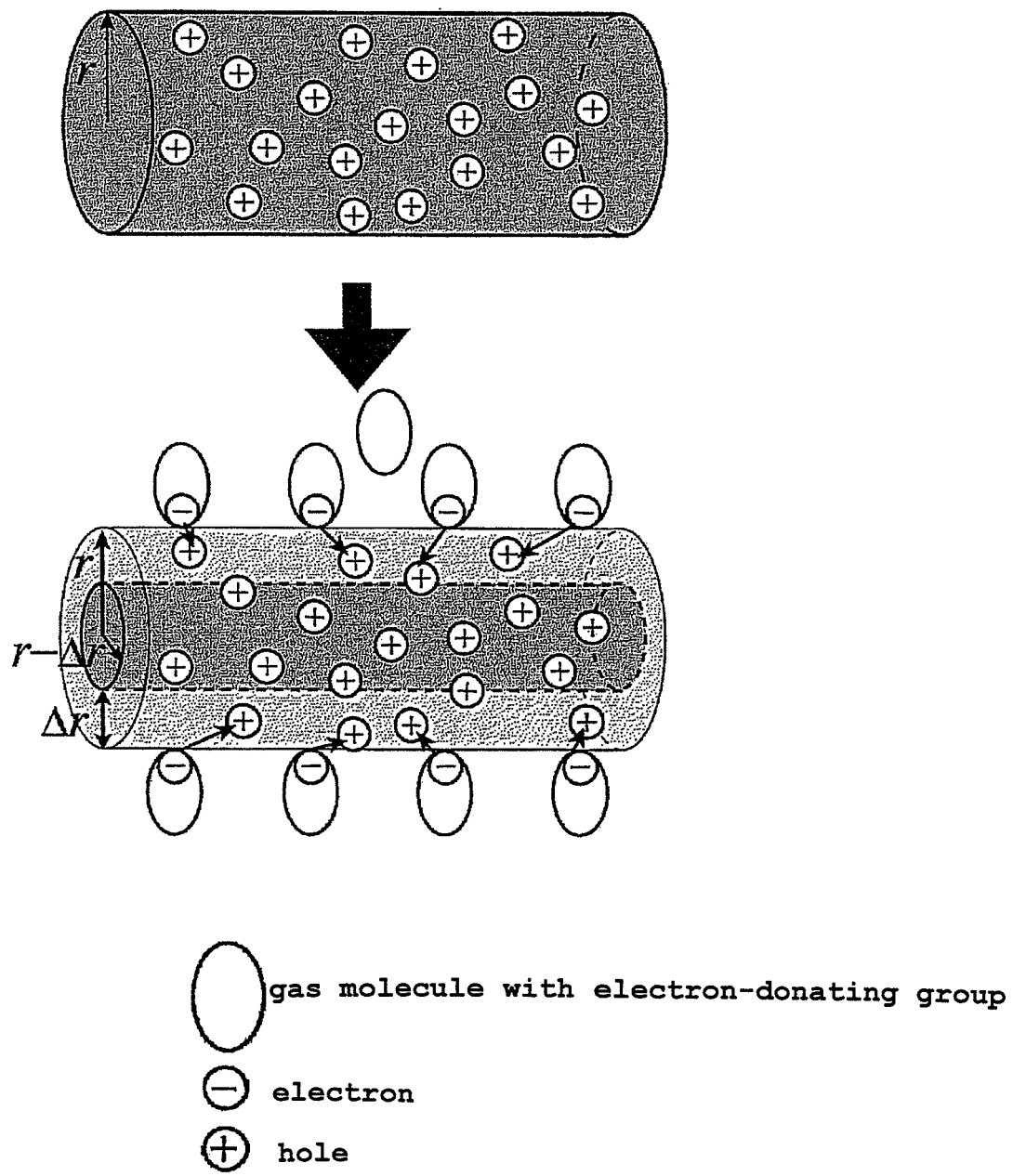
FIG. 3 is a schematic diagram of the mechanism of decrease of the current value flowing through a selenium nanowire (principle of gas sensing).

The mechanism of decrease of the value of current flowing through a selenium nanowire due to the contact (adsorption) of an organic gas with the selenium nanowire (principle of gas sensing) is shown in FIG. 3. Assuming a selenium nanowire having a radius r, since the selenium nanowire is a P-type semiconductor, the carrier is a hole. When an organic gas (gas molecule having electron-donating group) adsorbs to the surface of the selenium nanowire, electron is injected into the selenium nanowire, and the injected electron is bound to the hole in the selenium nanowire and disappears, thus lowering the hole density of the selenium nanowire. Since the injected electron is bound to the hole to decrease the radius of the selenium nanowire by $\Delta r$ in the Figure, the surface area of the selenium nanowire decreases and the current value decreases.

In this case, sensor sensitivity (S) is represented by the following formula.

$$I_0 = 2\pi r^2 J_{SC} \quad \text{[equation 1]}$$
$$I_m = 2\pi (r - \Delta r)^2 J_{SC}$$
$$S = (I_0 - I_m)/I_0 = \Delta I/I_0, \Delta I = I_0 - I_m$$
$$S = \frac{\Delta r}{r}\left(2 - \frac{\Delta r}{r}\right)$$

wherein r is a radius of a selenium nanowire, $I_0$ is an initial current value, $I_m$ is a minimum current value, and $J_{SC}$ is current density in space charge-limited current region.

The gas sensor of the present invention is constituted by forming an element structure comprising microcrystalline selenium disposed between two electrodes.

Figure 4:
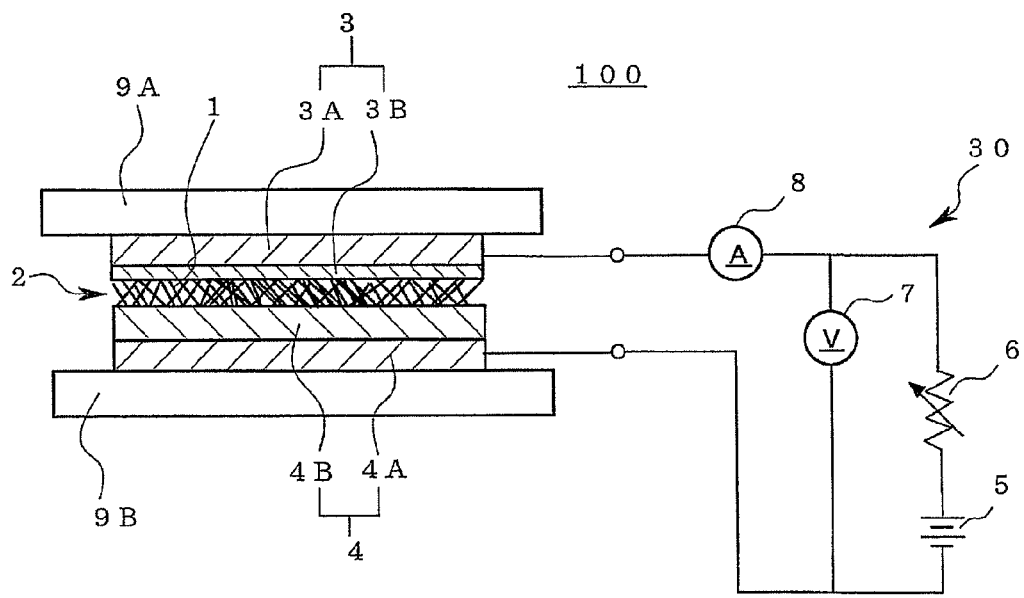
FIG. 4 is a schematic side view of one embodiment of the gas sensor of the present invention.

FIG. 4 is a schematic side view of one embodiment of the gas sensor of the present invention. As shown in gas sensor 100 therein, the gas sensor of the present invention contains a gas detector part 2 containing microcrystalline selenium 1, electrodes 3 and 4 facing each other with said gas detector part 2 in between, and an current value measurement part 30.

The gas detector part 2 is a structure part retaining microcrystalline selenium 1 and a gas in a contactable manner. In the example of FIG. 4, a selenium nanowire is used as microcrystalline selenium 1 and the selenium nanowire is fixed on one surface of a carbon tape (with thickness of generally about 50-160 μm) 4B by adsorption. The selenium nanowire can be fixed by adsorption onto carbon tape 4B by, for example, spraying a trace amount of selenium nanowire on carbon tape 4B and moderately compression boning same. In addition, the distance between electrodes can be fixed (fixing of elements) by confirming functionality of the sensor, and adhering bases 9A and 9B of the sensor with an adhesive (e.g., cyanoacrylate instant glue) and the like.

As carbon tape 4B, two-faced adhesive tapes containing a carbon powder as a conductive filler (e.g., carbon-base double-faced adhesive tape manufactured by Nisshin E M Corporation etc.) are preferably used. Using a double-coated adhesive type carbon tape, a selenium nanowire 1 can be maintained without being scattered on one surface of carbon tape 4B, the selenium nanowire can be maintained by being stuck into the adhesive face of the carbon tape 4B and, in some cases, the selenium nanowire 1 penetrates the carbon tape 4B to be in contact with a substrate electrode 4A, whereby the electric connection between the selenium nanowire and the electrode can be stably and certainly formed. In addition, since carbon tape 4B is elastic, the contact between the selenium nanowire and the electrode can be stably maintained even when they are under vibration from the outside.

Even when microcrystalline selenium consisting of monoclinic polyhedron is used as microcrystalline selenium 1, a gas detector part 2 is constituted by retaining microcrystalline selenium in the same manner as in the embodiment of a selenium nanowire.

Electrodes 3 and 4 can be formed from a material used for forming a conventional conductive electrode, such as gold, silver, copper, aluminum, nickel, ITO (indium tin oxide), carbon and the like. In the example of FIG. 4, an electrode 3 on the side to be in contact with microcrystalline selenium (selenium nanowire) 1 is constituted with a gold thin film 3B to be in contact with microcrystalline selenium (selenium nanowire) 1 and a substrate electrode (copper plate) 3A carrying said gold thin film 3B on the surface thereof, and an electrode 4 on the side retaining microcrystalline selenium (selenium nanowire) 1 is constituted with a carbon tape 4B and a substrate electrode (copper plate) 4A carrying said carbon tape 4B on the surface thereof. The gold thin film 3B is provided for improving conductivity and preventing degradation of conductivity due to oxidation of copper face.

The current value measurement part 30 contains a power source 5, a variable resistance 6 that adjusts power of power source 5, a voltmeter 7 that measures voltage applied between electrodes 3 and 4, and an ammeter 8 that measures the value of current flowing through the gas detector part 2 between electrodes 3 and 4.

In gas sensor 100 which is one of such embodiments, epoxy resin bases 9A, 9B are set on the outside of electrodes 3, 4, and bases 9A, 9B are formed to enhance rigidity and insulation property of the element structure and to fix the element as a whole (device fabrication). That is, the distance between electrodes can be fixed (fixing of device) by adhering bases 9A, 9B of the sensor with an adhesive (e.g., cyanoacrylate instant glue) and the like after confirmation of the functionality of the sensor.

Figure 5:
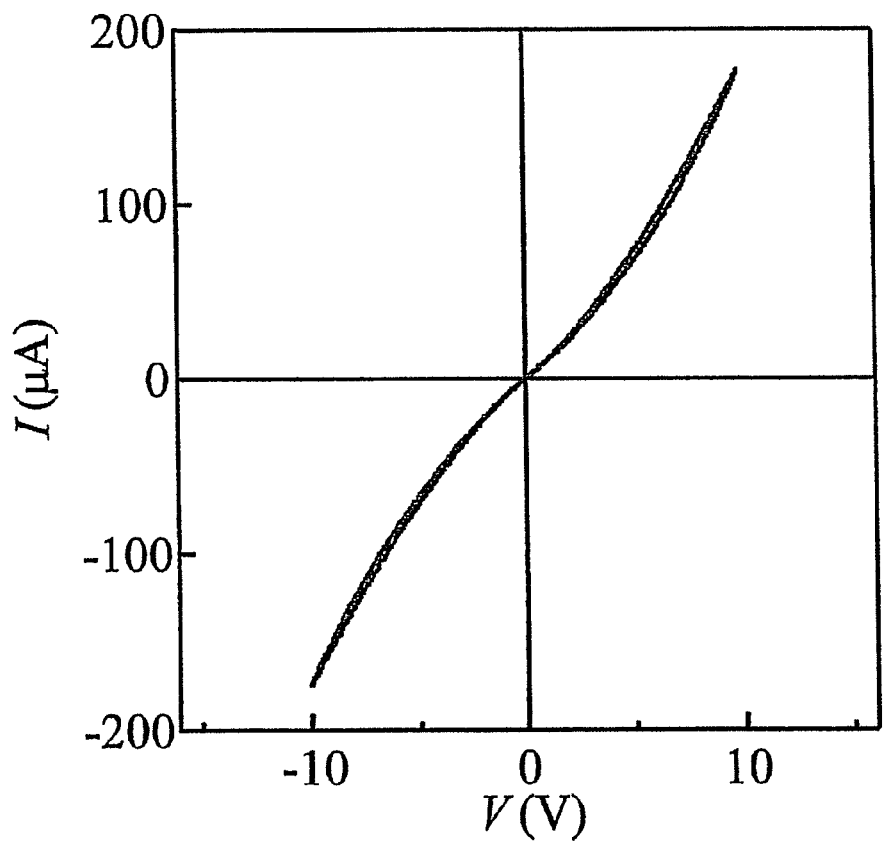
FIG. 5 is a drawing showing the voltage-current characteristics of the gas sensor of the present invention.
Figure 6:
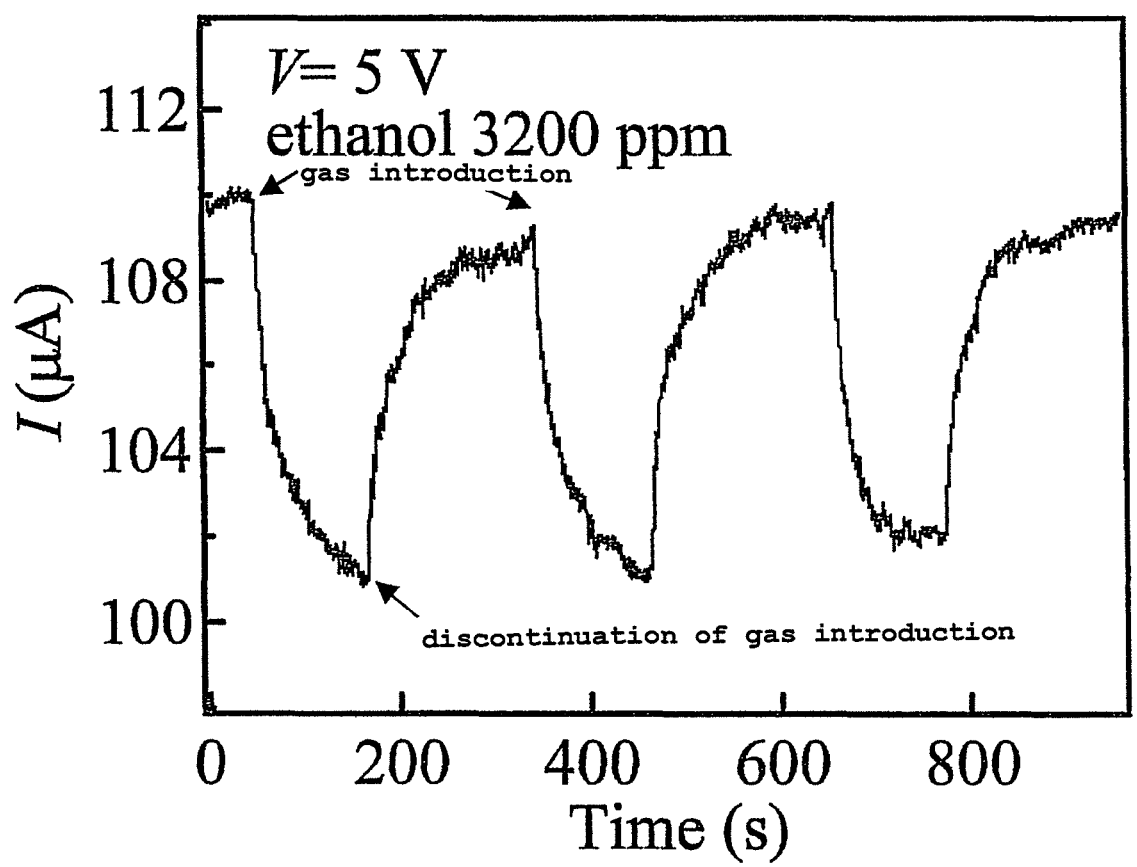
FIG. 6 is a drawing showing the sensitivity characteristics of the gas sensor of the present invention to ethanol gas.

The gas sensor of the present invention is generally activated as a sensor by applying an about 1-15V voltage to two opposing element electrodes 3, 4 with a distance between electrodes (d) being about 20-30 μm. For example, when 5V is applied, a constant current of about 40-120 μA flows through a gas detector part 2. The distance between electrodes (d) here is the distance between carbon tape 4B and gold thin film 3B, which corresponds to the thickness of a thin layer of an aggregate of microcrystalline selenium (microcrystalline selenium layer) in the gas detector part. When the gas detector part 2 is exposed to an organic gas, the current value decreases, and when the contact of the organic gas with the gas detector part 2 disappears, the current value restores to the original state. For example, FIG. 5 shows voltage-current characteristics of a gas sensor using a selenium nanowire (thickness: 23.3 nm, length: 4 μm) as a microcrystalline selenium 1 at room temperature in the air, and FIG. 6 shows current value change when 5V fixed voltage is applied to electrodes 3, 4 and 5L of air containing 100 μL of ethanol is intermittently contacted with the gas detector part 2. The 5V driving corresponds to the operation in batteries, and other voltage can be used for driving.

The behavior of current value change at a fixed voltage varies depending on the kind of an organic gas to be in contact with the gas detector part 2. Therefore, using the gas sensor of the present invention, the kind of an organic gas can be distinguished by observing such current value change and from the difference in the magnitude of current value change at a fixed voltage.

Figure 7:
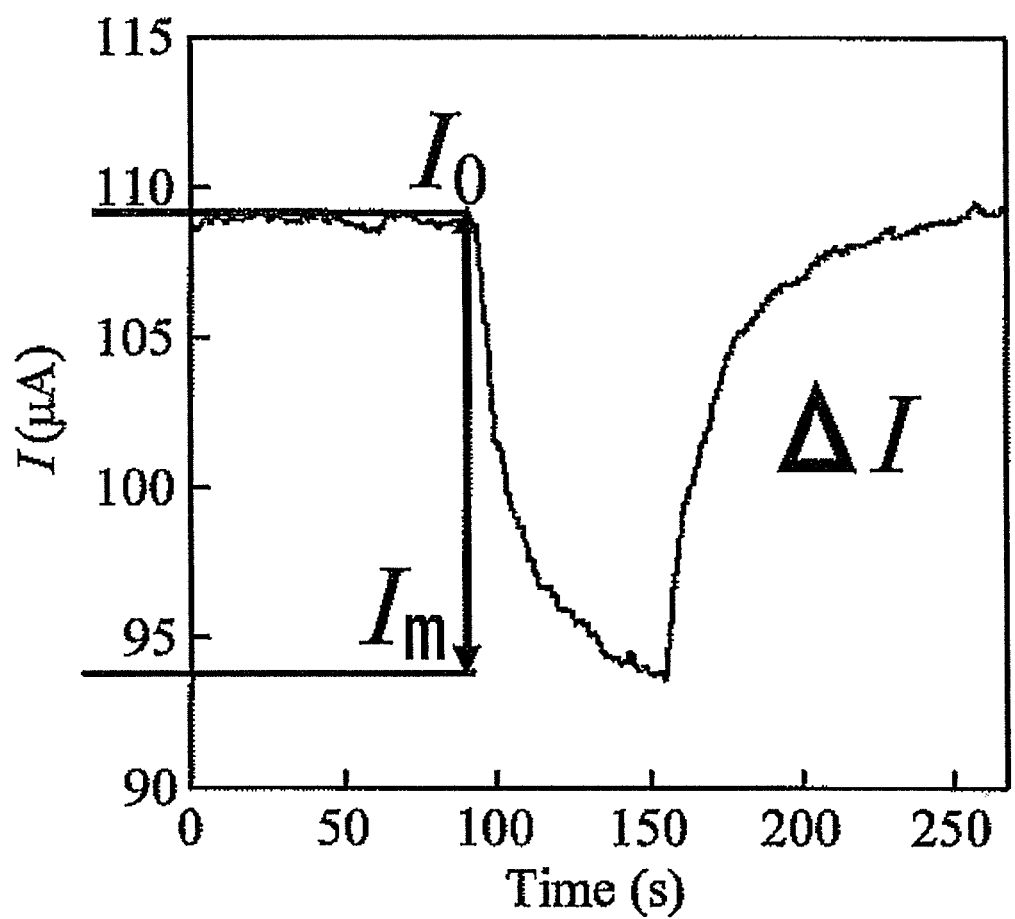
FIG. 7 is a partially enlarged view of FIG. 6.

FIG. 7 is a partially enlarged view of FIG. 6. $I_0$ in the Figure is an initial value of current flowing through a gas detector part 2 before contact with an organic gas (ethanol gas) and $I_m$ shows a minimum electric current value, and $\Delta I$ shows an amount of current value change.

Sensor sensitivity (S) of the gas sensor of the present invention is represented by the following formula.

$$S=(I_0-I_m)/I_0=\Delta I/I_0 \quad \text{[equation 2]}$$

Sensor sensitivity (S) is obtained by normalizing an amount of current value change $\Delta I=(I_0-I_m)$ due to organic gas to the initial current value I0.

A sensor shows a typical response to a change in the concentration of an organic gas. Therefore, as is clear from the below-mentioned Experimental Examples, since sensor sensitivity $S=\Delta I/I_0$ varies depending on the concentration of an organic gas in the gas to be in contact with the gas detector part 2, the concentration of the organic gas can be detected.

As is clear from the below-mentioned Experimental Examples, sensor sensitivity (S) shows a different amount of current value change ($\Delta I$), which is an amount of current value change on contact with a high concentration (100% concentration) of an organic gas (saturation sensitivity), depending on the kind of the organic gas. Utilizing this, therefore, the organic gas can be distinguished.

As is clear from the below-mentioned Experimental Examples, moreover, since an amount of current value change ($\Delta I$) and the relaxation time thereof (i.e., time necessary for reaching the maximum value of $\Delta I$ or time when $\Delta I$ decreases (relaxation time ($\tau_r$))) show correlation between different organic gases, using the difference in the relaxation time ($\tau_r$) as an index, an organic gas can be distinguished. That is, using the difference in the relaxation time ($\tau_r$) as an index, gaseous species can be distinguished from the difference in the temporal characteristic of the magnitude of current value change at a fixed voltage.

Alternatively, it is also possible to automatically judge detection and identification of an organic gas by collecting, as the standard data for every organic gas, saturation sensitivity (amount of current value change ($\Delta I$) at 100% concentration) and amounts of current value change at various gas concentrations, and incorporating, in a gas sensor, a judging apparatus (not shown) that inputs measured current values from an ammeter 8 into a microcomputer housing the standard data in memory.

When a selenium nanowire is used as a gas detector part 2 in the gas sensor of the present invention, in an embodiment where the thickness direction of the nanowire is mainly utilized for gas detection (electric conductivity), the electric conductivity in the overlapping direction of the nanowire is the main contribution, and the sensor sensitivity can be increased by utilizing the clearance between wires produced by the manner of overlapping of the wire. Therefore, in such embodiment, a smaller thickness (D) of the selenium nanowire tends to increase the amount of decrease of the electric current (sensitivity) due to the contact of an organic gas with the gas detector part 2. Thus, in such embodiment, the thickness (D) of the selenium nanowire is preferably not more than 500 nm, more preferably not more than 300 nm. While the lower limit is not particularly limited, it is preferably not less than several nm. On the other hand, the length (L) of the selenium nanowire is longer the better so that the wire will overlap. Therefore, the aspect ratio (L/D) is preferably not less than 5, more preferably not less than 10, particularly preferably not less than 15. While the upper limit is not particularly limited, it is preferably not more than 50, more preferably not more than 30.

On the other hand, in an embodiment where the length direction of a selenium nanowire is mainly utilized for gas detection (electric conduction), the length (L) of the selenium nanowire is determined according to the distance between electrodes, and is preferably equivalent to or a little longer than the distance between electrodes, that is, when the distance between electrodes is d, about $d+0-d+\sqrt{2}d$ μm. As the length of the selenium nanowire increases, the contribution of the electric conductivity in the wire thickness direction due to overlapping of the nanowire tends to increase.

The thickness (D) and length (L) of the selenium nanowire in the present invention are obtained by taking an SEM photograph, measuring the thickness and length of plural selenium nanowires (sample number: 50) from the photograph image, and selecting the peak values of distribution in each distribution graph.

When microcrystalline selenium consisting of monoclinic polyhedron is used as a gas detector part 2 in the gas sensor of the present invention, an average particle size thereof is preferably 1-10 μm. The average particle size is obtained by taking an SEM photograph, measuring the particle size of plural particles (sample number: 50) from the photograph image, and selecting the peak value of distribution in the distribution graph obtained therefrom.

In the gas sensor of the present invention, the area of the opposing surfaces of element electrodes 3 and 4 in the gas detector part 2 may be about 0.5—several mm$^2$, preferably about 1 mm$^2$. The amount of microcrystalline selenium placed between electrodes 3 and 4 may be an ultratrace amount of about 20-100 μg/mm$^2$, preferably about 50 μg/mm$^2$.

In the gas sensor 100 of the above-mentioned one embodiment, the gas detector part 2 has a constitution where a selenium nanowire 1 is fixed by adsorption to a carbon tape 4B fixed by adhesion to one electrode 4A. It can also be constituted by applying a selenium nanowire developed in an organic solvent to an electrode surface of one electrode 4 to allow adhesion thereto, or applying a selenium nanowire developed in an organic solvent to an insulated substrate to allow adhesion thereto, or fixing a selenium nanowire on an insulated substrate with a resin such as poly(methyl methacrylate) (PMMA) and the like, and placing a pair of comb-shaped electrodes having teeth opposedly set such that the teeth of one electrode are positioned at the clearance in the teeth of the other electrode.

The organic gas in the present invention is a volatile organic compound whose influence on the environment and human body is concerned. Examples thereof include methane, ethane, n-butane, isobutane, 2,2-dimethylbutane, 2,3-dimethylbutane, n-pentane, 2-methylpentane, 2,4-dimethylpentane, n-hexane, 3-methylhexane, n-heptane, 3-methylheptane, nonane, decane, undecane, methylcyclopentane, cyclohexane, methylcyclohexane, ethylcyclohexane, bicyclohexyl, propylene, cis-2-butene, trans-2-butene, 2-methyl-2-butene, 2-methyl-1-butene, 1,3-butadiene, isoprene, cis-2-pentene, trans-2-pentene, 1-heptene, dipentene, benzene, toluene, xylene, 1,3,5-trimethylbenzene, ethylbenzene, cumene, styrene, naphthalene, tetralin, chloromethane, dichloromethane, chloroform, methyl bromide, chloroethane, 1,2-dichloroethane, trichloroethane, trichloroethylene, tetrachloroethylene, tetrafluoroethylene, vinyl chloride, 1,1-dichloroethylene, n-propylbromide, 1,2-dichloropropane, allyl chloride, chlorobenzene, o-dichlorobenzene, methanol, ethanol, isopropanol, n-butanol, isobutanol, ethylene glycol, benzyl alcohol, phenol, methylmercaptan, ethylene glycol monomethylether, ethylcellosolve, isopropylcellosolve, butylcellosolve, propylene glycol monomethylether, oxidation propylene, ethyleneoxide, epichlorohydrin, tetrahydrofuran, 1,4-dioxane, formic acid methyl, ethyl acetate, propyl acetate, butyl acetate, vinyl acetate, methylcellosolveacetate, ethylcellosolveacetate, propylene glycol monomethyletheracetate, propionic acid, acrylic acid, methyl acrylate, methyl methacrylate, acetone, methylethyl ketone, methylisobutylketone, methyln-butylketone, methylamylketone, cyclopentanone, cyclohexanone, isophorone, dimethyl sulfoxide, trimethylamine, triethylamine, cyclohexylamine, pyridine, piperidine, formaldehyde, acetaldehyde, acetonitrile, acrylonitrile, N,N-dimethylformamide, N-methyl-2-pyrrolidone and the like. Among these, a volatile organic compound such as benzene, toluene, pyridine, piperidine, acetone, ethanol, methanol, iosbutanol, formaldehyde, phenol, ethyl acetate, styrene, trimethylamine, n-hexane, cyclohexane and the like, which shows a relative permittivity at room temperature of 1.0-40.0 (particularly 1.0-38.0) can be detected with particularly high sensitivity.

EXAMPLES

The present invention is explained in more detail in the following by referring to Examples, which are not to be construed as limitative.

Example 1

A commercially available granular amorphous selenium (purity: 99.9999%, Rare Metallic Co., Ltd.) was milled into a fine powder in a mortar. The granulated amorphous selenium was irregular particles having a particle size of 20-30 μm. This amorphous selenium fine powder (about 0.3 g) was added to acetone (7 mL, relative permittivity: 20.7) in a glass tube, and the mixture was left standing at room temperature for 10 days. In addition, similarly, an amorphous selenium fine powder (about 0.3 g) was added to benzene (7 mL, relative permittivity: 2.3) in a glass tube, and the mixture was left standing at room temperature for 10 days.

The form of the amorphous selenium fine powder, the resultant product in acetone and the resultant product in benzene was observed with a scanning electron microscope (SEM, JOEL JXA-8900). In addition, the crystal structures thereof were analyzed by an X-ray diffraction apparatus (manufactured by Rigaku Corporation, RINT 2500).

FIG. 1(a) is an SEM photograph of amorphous selenium, FIG. 1(b) is an SEM photograph of the resultant product in acetone, and FIG. 1(c) is an SEM photograph of the resultant product in benzene. It was known from FIG. 1(b) that the resultant product in acetone was a nanowire form having a nano-sized thickness (258 nm) and a length of 4.3 μm. It was known from FIG. 1(c) that the resultant product in benzene was polyhedron fine particles having an average particle size of about 10 μm.

FIG. 2(a) is an X-ray diffraction pattern of an amorphous selenium, FIG. 2(b) is an X-ray diffraction pattern of the nanowire form produced in acetone, and FIG. 2(c) is an X-ray diffraction pattern of the polyhedron fine particles produced in benzene. The X-ray diffraction pattern of FIG. 2(b) shows hexagonal selenium, and the X-ray diffraction pattern of FIG. 2(c) shows monoclinic selenium. The moderate part in the X-ray diffraction pattern of FIG. 2(c) is of amorphous selenium.

The above results reveal that amorphous selenium contacted with an organic solvent undergoes self-crystal growth due to a catalytic action of the organic solvent to give nanowire-like hexagonal microcrystalline selenium having a thickness of a nano size, that is, a selenium nanowire, or granular monoclinic microcrystalline selenium made of polyhedron particles.

Example 2

A gas sensor shown in FIG. 4 was produced using the selenium nanowire (nanowire hexagonal microcrystalline selenium with thickness 258 nm and length 4.3 μm) and granular microcrystalline selenium (granular monoclinic microcrystalline selenium having an average particle size of about 10 μm), which were obtained in Example 1, and the amorphous selenium fine powder (ground product) used in Example 1.

That is, an ultratrace amount (about 50 μg) of a selenium nanowire was uniformly adsorbed on one surface of a carbon tape (length×width×thickness of 1.0 mm×1.0 mm×0.16 mm, manufactured by Nisshin EM Corporation, carbon double-faced adhesive tape) with a wooden extra fine stick. The thickness of the carbon tape after adsorption of the selenium nanowire was about 75 μm, and that of a selenium nanowire adsorption layer was 23 μm. The selenium nanowire was weighed with Sartorius Basic plus balance BP221S manufactured by SARTORIUS K.K. One surface of the carbon tape, which is on the opposite side from the surface on which the selenium nanowire was adsorbed, was supported with a first electrode plate made of a copper plate (length×width×thickness of 1.0 mm×1.0 mm×35 μm). On the other hand, a second electrode board made of a laminate conductive board wherein a gold thin film having a thickness of about 0.02-0.03 μm was formed on one surface of a copper plate (length×width×thickness of 1.0 mm×1.0 mm×35 μm) by a vapor deposition method using sputtering was prepared. The gold thin film was contacted with fibrous microcrystalline selenium maintained by adsorption on one surface of the carbon tape, and disposed opposite to the first electrode board (distance between electrodes: 23 μm). A circuit containing an ammeter, a voltmeter and a power source between both electrodes was formed to complete a gas sensor.

In the same manner, a gas sensor apparatus using granular microcrystalline selenium (monoclinic system) in a gas detector part and a gas sensor apparatus using an amorphous selenium fine powder (ground product) in a gas detector part were produced.

Figure 8:
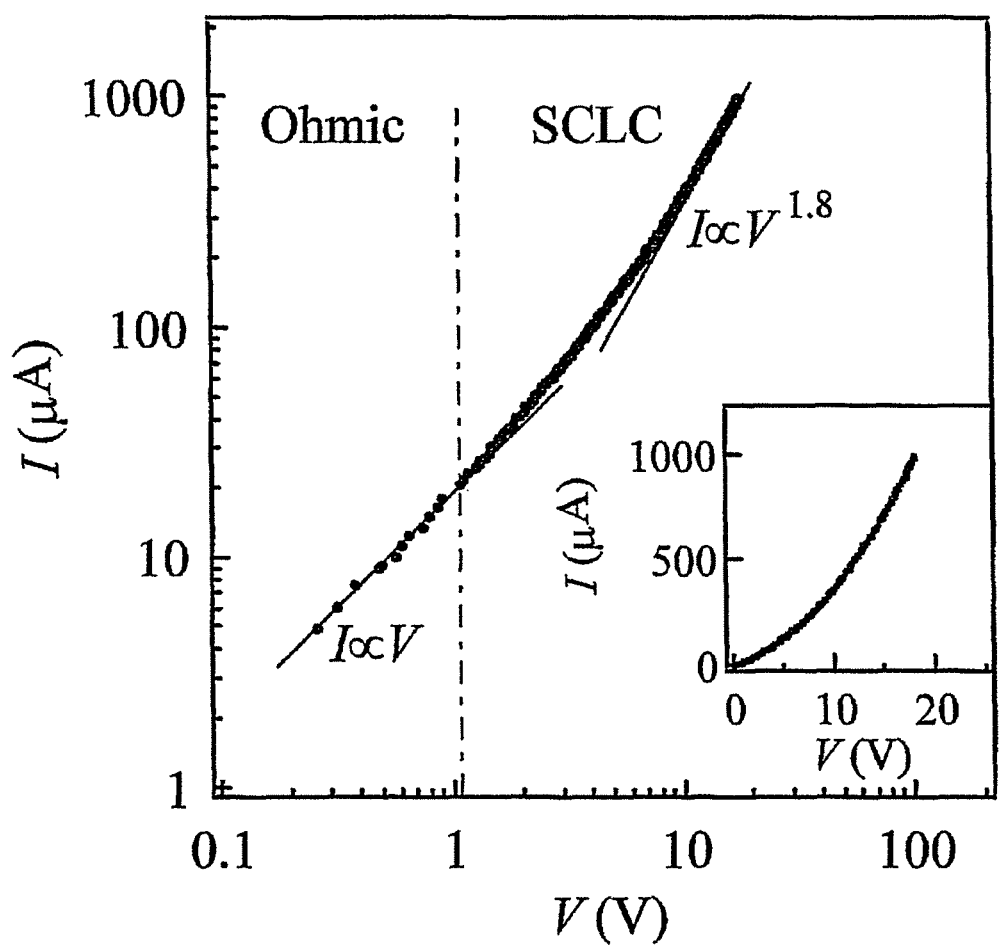
FIG. 8 is a double-logarithmic graph of current-voltage characteristics (I-V property) of a gas sensor using a selenium nanowire.

FIG. 5 shows the current-voltage characteristics (I-V property) of the thus-produced gas sensor apparatus. From this Figure, it was found that a selenium nanowire (nanowire-like hexagonal microcrystalline selenium) shows voltage-current characteristics due to an electric conductivity mechanism as a P-type semiconductor intrinsic to selenium. In addition, both granular monoclinic microcrystalline selenium and amorphous selenium fine powder showed similar voltage-current characteristics, though the current value was small. In addition, FIG. 8 shows a double-logarithmic graph of current-voltage characteristics (I-V property) of a gas sensor, using a selenium nanowire in a gas detector part, at a voltage of 0-about 20 V. Ohmic features are observed at a voltage of up to about 1 V, and the voltage region higher than that is a space charge limited current (SCLC) region showing nonlinearity. The electric current density ($J_{SC}$) of the SCLC region is represented by the following formula:

$$J_{SC} = \zeta(D/L)\frac{\epsilon_{Se}\mu_{Se}V^2}{d^3} \quad \text{[equation 3]}$$

wherein $\epsilon_{Se}$ is a permittivity of hexagonal selenium, $\mu_{Se}$ is mobility of hexagonal selenium, $\zeta(D/L)$ is a proportional constant given by a function of aspect ratio (D/L) (when D/L≫1 (general bulk crystal), $\zeta(D/L)=9/8$), d is a distance between electrodes and V is a voltage.

Then, 5 L of air containing 100 μL of ethanol (test gas) was contacted with a gas detector part of a gas sensor apparatus, through which an electric current was flown at fixed voltage 5V, and current value change was observed. For the measurement, ethanol was placed in a gas bag with a syringe, a given amount of air was charged therein with a mini pump (SIBATA MP-Σ30N (manufactured by SIBATA SCIENTIFIC TECHNOLOGY LTD.)) to give a test gas, and the test gas was conversely discharged without contact from the gas bag with a mini pump at a constant flow rate from the nozzle toward the detection part of the gas sensor.

FIG. 6 shows current value change of the gas sensor apparatus using selenium nanowire (nanowire-like hexagonal microcrystalline selenium) in the gas detector part due to the organic gas (ethanol gas). It is clear from this Figure that a selenium nanowire has high reaction sensitivity to organic gas, the resistance increases rapidly to decrease current value upon contact with an organic gas, and the decreased amount of the current is high. Also, it is clear that the current value increases rapidly when the contact with the organic gas is ceased, thereby affording a sensor element with high sensitivity.

Experimental Example 1

Using the gas sensor apparatus prepared above, an organic gas was contacted with a gas detector part through which an electric current was flown at room temperature and fixed voltage 5V, and current value change ($I/I_0$) due to the organic gas were examined. Here, $I_0$ is a constant current value before contacting the organic gas with the gas detector part, and I is a current value after contacting the organic gas with the gas detector part. As the organic gas, acetone and benzene were used, and the organic gas was contacted with the gas detector part by impregnating a cotton swab with the organic solvent (acetone, benzene), bringing the cotton swab near to the gas detector part, and allowing contact of each gas (acetone 5400 ppm, benzene 220 ppm) volatilized from the cotton swab with the gas detector part for 120 seconds. The concentration of the organic gas was measured by a gas detector tube manufactured by GASTEC CORPORATION. The method including impregnating a cotton swab with an organic solvent, bringing the cotton swab near to a gas detector part, and measuring the organic gas volatilized from the cotton swab (that is, method of passively adsorbing organic gas to selenium nanowire) corresponds to a gas detection operation by a gas sensor in an actual environment where an organic gas is floating in the air.

Figure 9:
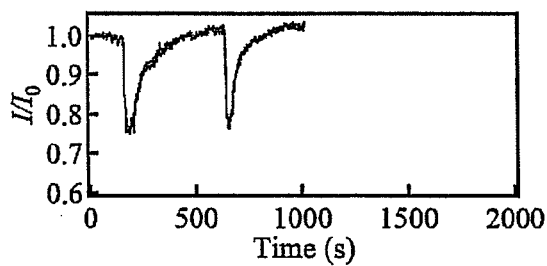
FIG. 9 shows sensing properties of a gas sensor using a selenium nanowire, a gas sensor using granular microcrystalline selenium (monoclinic system) and a gas sensor using an amorphous selenium fine powder.
Figure 9:
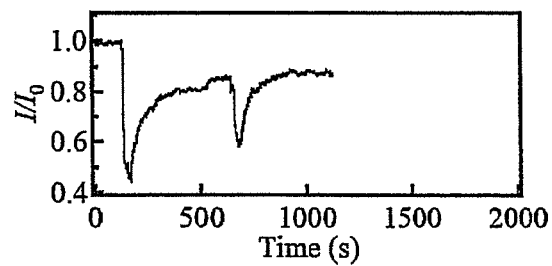
Figure 9:
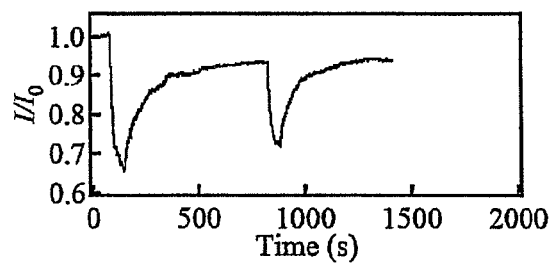
Figure 9:
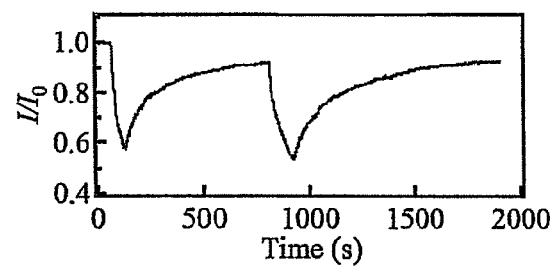
Figure 9:
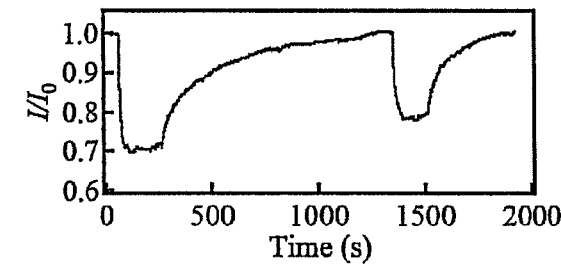
Figure 9:
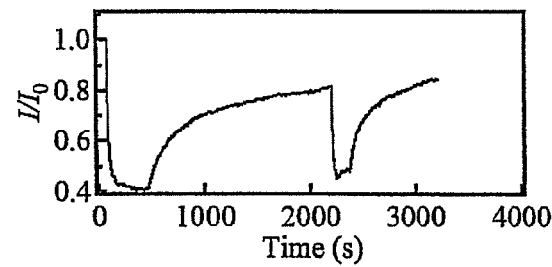

The results are shown in FIG. 9. In the Figure, the chart in the upper panel shows sensitivity property of an apparatus using selenium nanowire (nanowire-like hexagonal microcrystalline selenium) in a gas detector part, the chart in the middle panel shows sensitivity property of an apparatus using granular monoclinic microcrystalline selenium in a gas detector part, and the chart in the lower panel shows sensitivity property of an apparatus using amorphous selenium particles in a gas detector part.

From FIG. 9, it is clear that granular monoclinic microcrystalline selenium and selenium nanowire (nanowire-like hexagonal microcrystalline selenium) show high reaction sensitivity with an organic gas as compared to amorphous selenium particles, particularly, selenium nanowire (nanowire-like hexagonal microcrystalline selenium) shows extremely high reaction sensitivity with an organic gas (high decrease amount of current), and very short relaxation time (high current decrease rate).

Example 3

In the same manner as in Example 1 except that (R)-(−)-2-butanol (relative permittivity: 16.72) was used instead of acetone, an amorphous selenium fine powder (ground product) was immersed in (R)-(−)-2-butanol at room temperature for 10 days, and the crystal structure thereof was analyzed by an X-ray diffraction apparatus. As a result, it was hexagonal microcrystalline selenium. The resultant product in (R)-(−)-2-butanol was dried and placed in an acetone solution. Entangled microcrystalline selenium was disentangled by ultrasonication, and microcrystalline selenium floating in the acetone solution was observed with SEM. As a result, it was selenium nanowire (nanowire hexagonal microcrystalline selenium) having a thickness of 175 nm and a length of 5.40 μm.

Example 4

In the same manner as in Example 1 except that (R)-(−)-2-heptanol (relative permittivity: 9.25) was used instead of acetone, an amorphous selenium fine powder (ground product) was immersed in (R)-(−)-2-heptanol at room temperature for 2 years, and the crystal structure thereof was analyzed by an X-ray diffraction apparatus. As a result, it was hexagonal microcrystalline selenium. The resultant product in (R)-(−)-2-heptanol was dried and placed in an acetone solution. Entangled microcrystalline selenium was disentangled by ultrasonication, and microcrystalline selenium floating in the acetone solution was observed with SEM. As a result, it was selenium nanowire (nanowire hexagonal microcrystalline selenium) having a thickness of 470 nm and a length of 2.48 μm.

Example 5

The amorphous selenium fine powder (ground product) used in Example 1 was placed in a desiccator filled with saturated acetone vapor, and left standing at room temperature for 40 days. The crystal structure of the resultant product in the desiccator was analyzed by an X-ray diffraction apparatus. As a result, it was hexagonal microcrystalline selenium. The resultant product in the desiccator was dried and the product was placed in an acetone solution. Entangled microcrystalline selenium was disentangled by ultrasonication, and microcrystalline selenium floating in the acetone solution was observed with SEM. As a result, it was selenium nanowire (nanowire hexagonal microcrystalline selenium) having a thickness of 275 nm and a length of 2.85 μm.

The following Table 1 shows the thickness (D) and length (L) of the selenium nanowires (nanowire-like hexagonal microcrystalline selenium) obtained in the above-mentioned Examples 1 and 3-5 along with the organic solvents used.

TABLE 1

| | organic solvent | relative permittivity (25° C.) | D (nm) | L (μm) | production time |
|---|---|---|---|---|---|
| Ex. 3 | (R)-(−)-2-butanol | 16.72 | 175 | 5.40 | 25° C., 10 days |
| Ex. 3 | acetone (in liquid) | 20.7 | 258 | 4.30 | 25° C., 10 days |
| Ex. 5 | acetone (in vapor) | 20.7 | 275 | 2.85 | 25° C., 40 days |
| Ex. 4 | (R)-(−)-2-heptanol | 9.25 | 470 | 2.48 | 25° C., 2 years |

R and S in parentheses of the organic solvent in the Table show optical chirality (R: clockwise, S: counter clockwise), and + and − show optical rotation (+: right, −: left).

Figure 10:
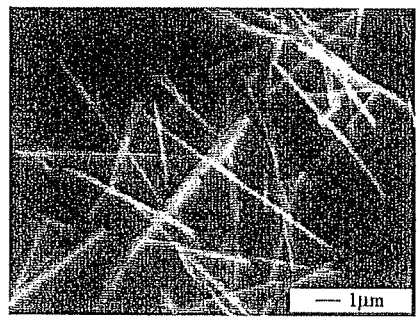
FIG. 10 shows SEM photographs of the selenium nanowires obtained in Examples 1 and 3-5.
Figure 10:
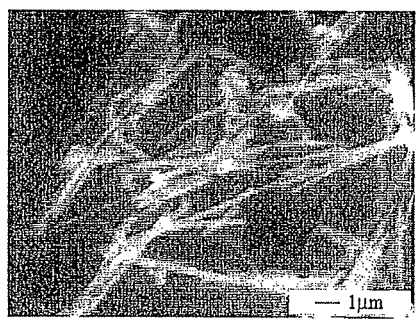
Figure 10:
Figure 10:

FIG. 10 is an SEM photograph of the selenium nanowires (nanowire-like hexagonal microcrystalline selenium) of Examples 1 and 3-5, (a) is an SEM photograph of the selenium nanowire of Example 3, (b) is an SEM photograph of the selenium nanowire of Example 1, (c) is an SEM photograph of the selenium nanowire of Example 5, and (d) is an SEM photograph of the selenium nanowire of Example 4.

Example 6

In the same manner as in Example 1 except that the following organic solvents were used instead of acetone, an amorphous selenium fine powder (ground product) was immerse in the organic solvents shown in the following Table 2 to prepare selenium nanowires. Using (R)-(−)-2-heptanol, a selenium nanowire with thickness (D) 565 nm and length (L) 3.75 μm was obtained, using (R)-(−)-2-butanol, a selenium nanowire with thickness (D) 274 nm and length (L) 3.25 μm was obtained, and using (R)-(+)-2-heptanol, a selenium nanowire with thickness (D) 233 nm and length (L) 3.75 μm was obtained. In addition, separately using three kinds of selenium nanowires with different thicknesses and in the same manner as above, three kinds of sensor apparatuses with different thicknesses of the selenium nanowire in the gas detector part were prepared.

The following Table 2 shows thickness (D) and length (L) of the obtained selenium nanowires (nanowire hexagonal microcrystalline selenium) together with the organic solvents used.

TABLE 2

| organic solvent | relative permittivity (25° C.) | D (nm) | L (μm) | production time |
|---|---|---|---|---|
| (R)-(−)-2-heptanol | 9.25 | 565 | 3.75 | 25° C., 2 years |
| (R)-(−)-2-butanol | 16.72 | 274 | 3.25 | 25° C., 10 days |
| (R)-(+)-2-heptanol | 9.25 | 233 | 3.75 | 25° C., 2 years |

Experimental Example 2

Using the three kinds of gas sensor apparatuses produced in Example 6, an organic gas was contacted with a gas detector part, through which an electric current was flown at a fixed voltage 5V, at room temperature, and the reaction sensitivity ($I/I_0$) to the organic gas was examined. Benzene was used as the organic gas, which was contacted with the gas detector part in the same manner as in Experimental Example 1, whereby the organic gas (220 ppm) was contacted with the gas detector part for 100-400 seconds. The results are shown in FIG. 11.

In the Figure, the upper panel is an SEM photograph and a sensitivity property chart of the selenium nanowire having a thickness (D) of 565 nm, the middle panel is an SEM photograph and a sensitivity property chart of the selenium nanowire having a thickness (D) of 274 nm, and the lower panel is an SEM photograph and a sensitivity property chart of the selenium nanowire having a thickness (D) of 233 nm.

Figure 11:
FIG. 11 shows the relationship between thickness of selenium nanowire and reaction sensitivity to an organic gas, together with SEM photographs of the selenium nanowires used.
Figure 11:
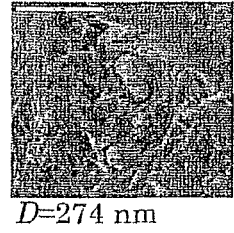
Figure 11:
Figure 11:
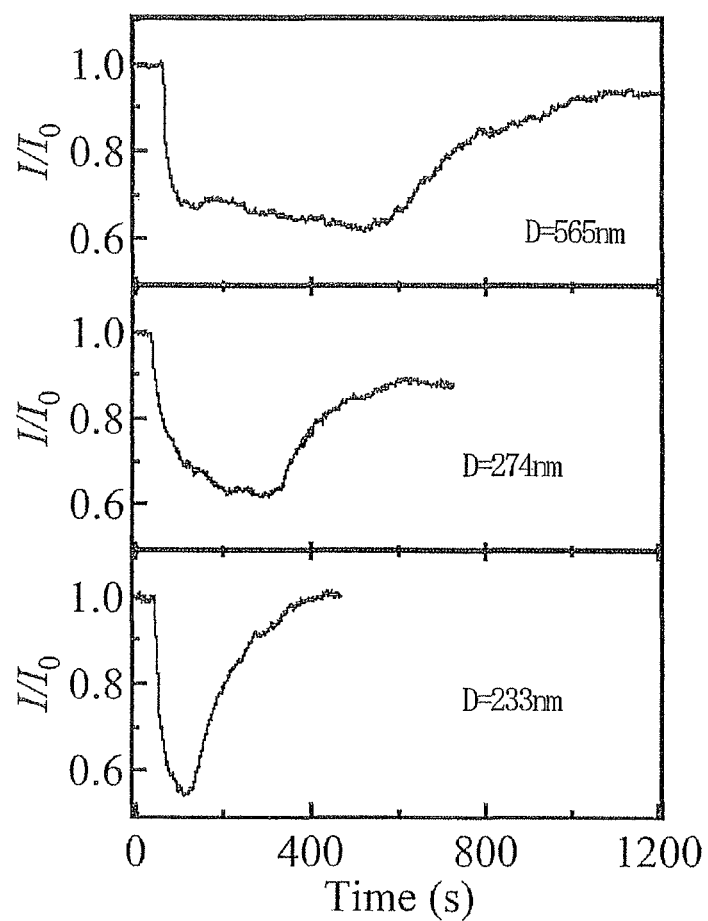

From FIG. 11, it is clear that a thinner selenium nanowire leads to higher reaction sensitivity to an organic gas (higher electric current decrease rate) and an extremely short reaction time (relaxation time). The main reason for such tendency in the thickness direction of the selenium nanowire is considered to be an increase of the surface area due to thinner nanowires. This can also be presumed from SEM images.

Experimental Example 3

Using gas sensors using the three kinds of selenium nanowires obtained in Example 6 in respective gas detector parts and commercially available organic solvents, an electric current at fixed voltage 10V was flown through a gas detector part and various organic gases (methanol, ethanol, 1-butanol, formaldehyde, acetone, pyridine, piperidine, benzene, toluene, cyclohexane, diethyl ether) were contacted with the gas detector part at room temperature. The relationship between the kind of the organic gas and sensor sensitivity (S) of the sensor was examined. As an experiment method, a method similar to Experimental Example 1 was performed for each organic gas. In addition, the relationship between the relative permittivity of an organic gas and the rate of current change ($\Delta I/I_0$), which shows sensor sensitivity (S), was examined. Since similar results were obtained in any apparatus, the results of the gas sensor apparatus using a selenium nanowire having a thickness (D) of 233 nm and a length (L) of 3.75 μm are shown as a representative example in FIG. 12.

The sensor sensitivity (S(N)) of a gas sensor apparatus using a selenium nanowire to the concentration (N) of a test gas can be shown by the following formula.

$$S(N) = A\xi\left(\frac{\epsilon_r - 1}{\epsilon_r + 2}\right)\left[2 - \xi\left(\frac{\epsilon_r - 1}{\epsilon_r + 2}\right)\right].$$ [equation 4]

$$\xi = (3V/d)N^n/N_m$$

wherein $\epsilon_r$ is a relative permittivity of organic gas (relative permittivity of stock solution of commercially available organic solvent), A is a contact efficiency of selenium nanowire and gas, V is a voltage, d is a distance between electrodes, N is a concentration, n is a power number, and $N_m$ is the concentration of a stock solution of a commercially available organic solvent.

From $2 \gg \xi(\epsilon_r-1)/(\epsilon_r+2)$, the sensor sensitivity can be shown by the following formula.

$$S(N)=S(N_m)N_x^n$$ [equation 5]

wherein $N_x$ is concentration N/Nm standardized by organic gas Nm.

Figure 12:
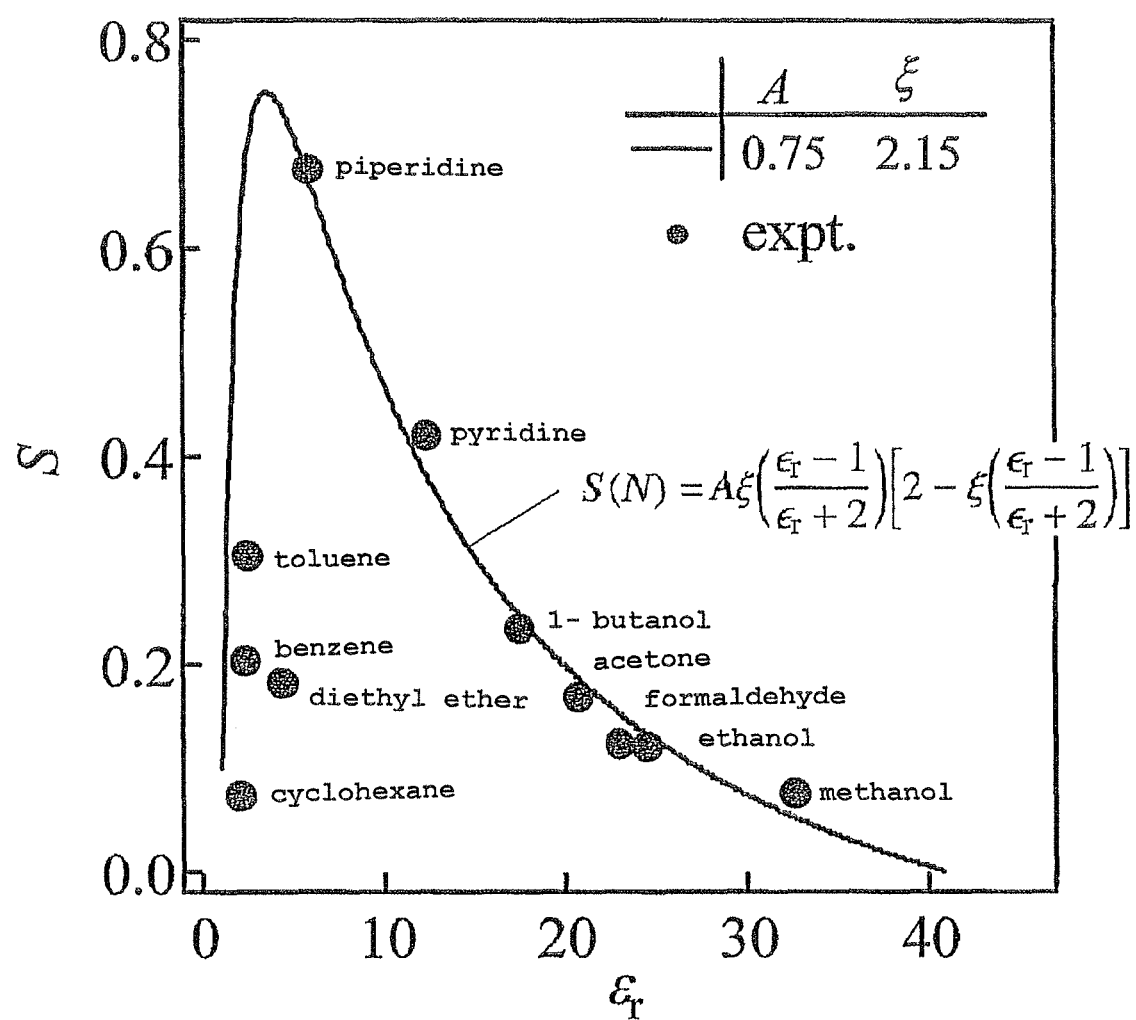
FIG. 12 shows the relationship between relative permittivity ($\epsilon_r$) and sensor sensitivity ($S=\Delta I/I_0$) of organic gases.

The curve in FIG. 12 shows the fitting of the above-mentioned formula [4] wherein A=0.75, $\xi$=2.15. When a high concentration of an organic gas is used, since the rate of current change ($\Delta I/I_0$), which is sensor sensitivity (S), varies depending on the difference in the relative permittivity due to the difference in the kind of the organic gas, the gas sensor of the present invention can also distinguish the kind of the organic gas.

Using each organic gas, the relationship between the rate of current change ($\Delta I/I_0$), which is sensor sensitivity (S), and the time of electric current change (=relaxation time ($\tau r$)) was examined. Since similar results were obtained in any apparatus, the results of the gas sensor apparatus using a selenium nanowire having a thickness (D) of 233 nm and a length (L) of 3.75 μm are shown as a representative example in FIG. 13.

Figure 13:
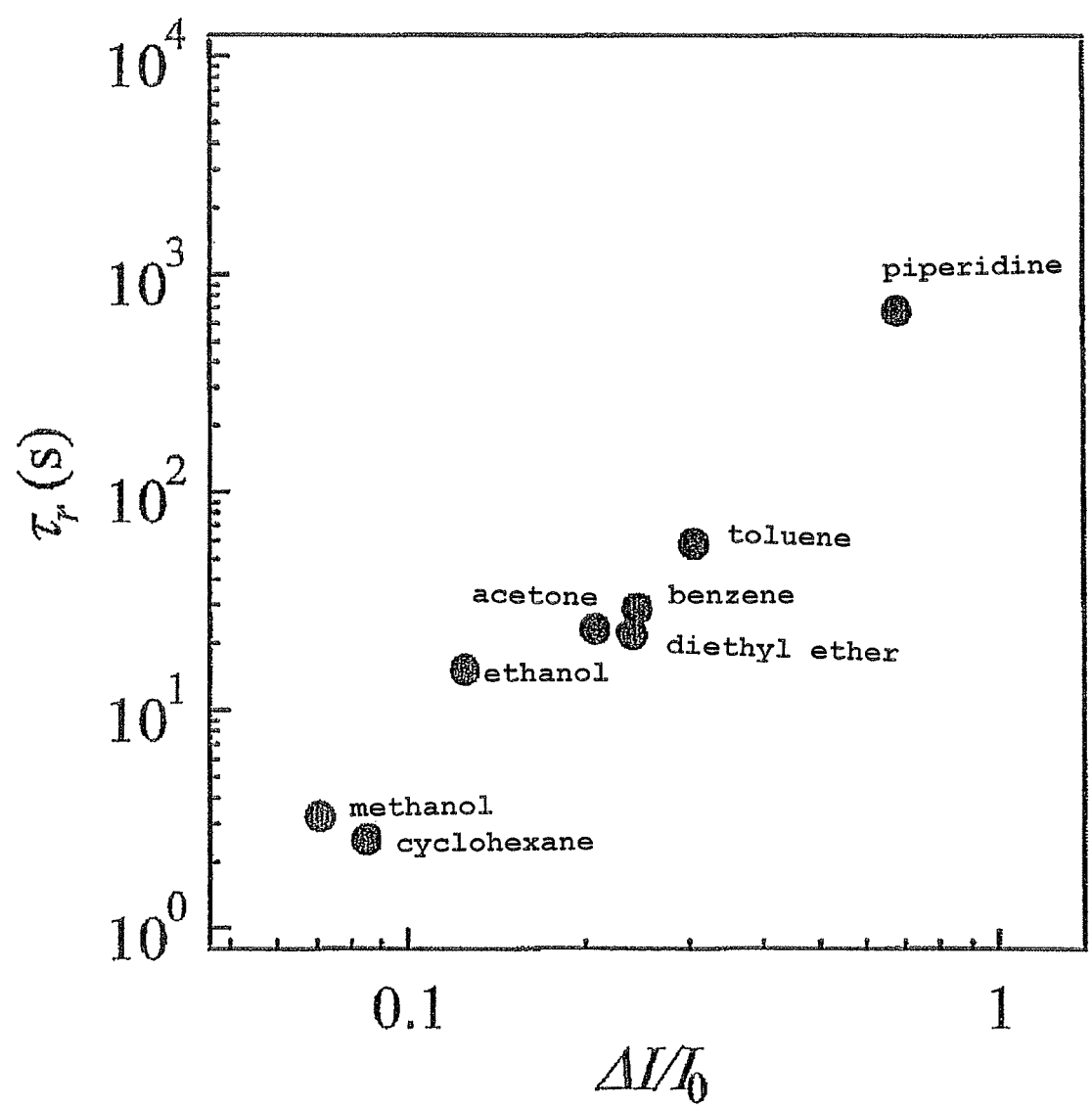
FIG. 13 shows the relationship between an amount of change in current (sensor sensitivity ($S=\Delta I/I_0$)) and relaxation time ($\tau_1$) of the amount of current change.

As is clear from FIG. 13, in the gas sensor of the present invention, since the amount of current change ($\Delta I$) due m to the contact of an organic gas with the gas detector part and the relaxation time ($\tau_r$) thereof show a correlation between different organic gases, the organic gas can also be distinguished by utilizing the difference in the relaxation time of the amount of current change (i.e., difference in temporal characteristic of the magnitude of current change at a fixed voltage).

Experimental Example 4

Using gas sensors using the three kinds of selenium nanowires obtained in Example 6 in respective gas detector parts, an electric current at fixed voltage 5V was flown through a gas detector part at room temperature and various test gases (air) having different contents of ethanol gas were contacted with the gas detector part, and the relationship between the concentration of ethanol gas in the test gas and the sensor sensitivity property was examined. The relationship between the concentration of ethanol gas in the test gas and the rate of current change ($\Delta I/I_0$), which is the ratio of the current value $I_0$ before contact of the test gas with the gas detector part and the amount of current value change ($\Delta I$) due to the contact of the test gas with the gas detector part was examined. Since similar results were obtained in any apparatus, the results of the gas sensor apparatus using a selenium nanowire having a thickness (D) of 233 nm and a length (L) of 3.75 μm are shown as a representative example in FIG. 14. In addition, similar tests were also performed for benzene gas, acetone gas and methanol gas. The tests were performed by adjusting the gas concentration of the alcohol gas (ethanol gas, methanol gas) by diluting alcohol, and the gas concentration of the acetone gas and benzene gas was adjusted by changing the distance between a cotton swab impregnated with an organic solvent (acetone, benzene) and the gas detector part within the range of 1 mm-5 mm. The gas concentration was measured by a gas detector tube manufactured by GASTEC CORPORATION.

Figure 14:
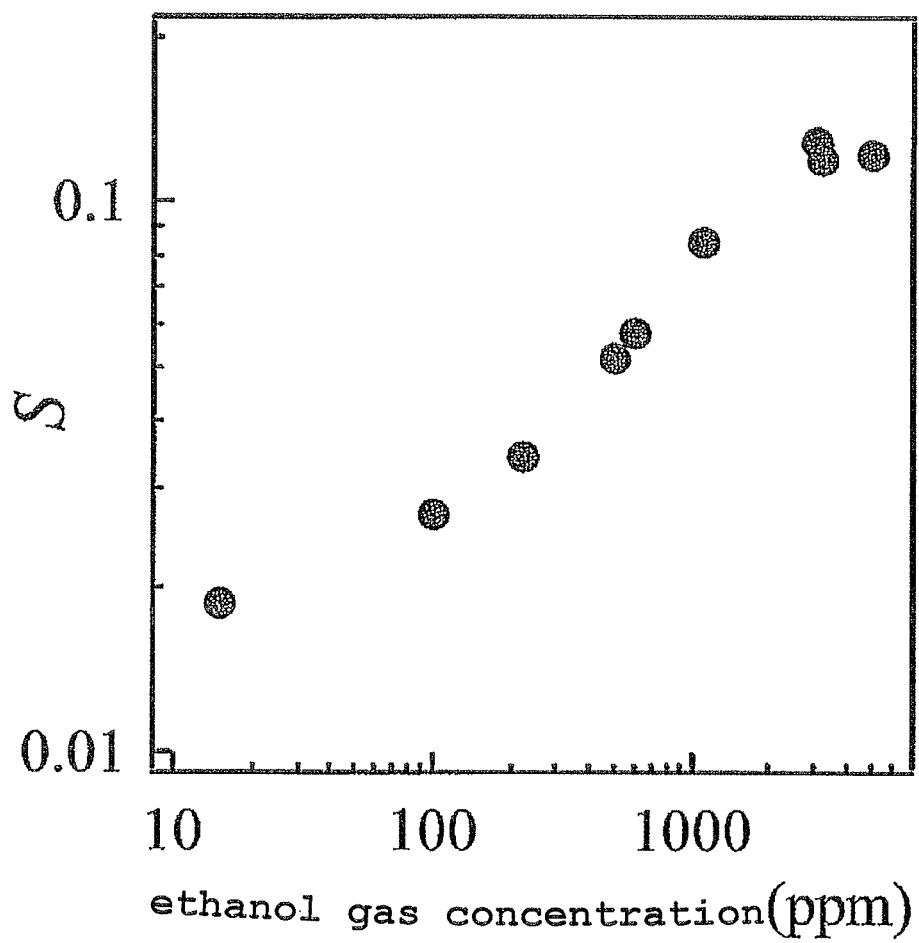
FIG. 14 shows the relationship (correlation) between ethanol gas concentration and sensor sensitivity ($S=\Delta I/I_0$) of the gas sensor of the present invention.

It is clear from FIG. 14 that the concentration of the organic gas in the test gas and the rate of current change ($\Delta I/I_0$), which is sensor sensitivity (S), show a correlation.

Figure 15:
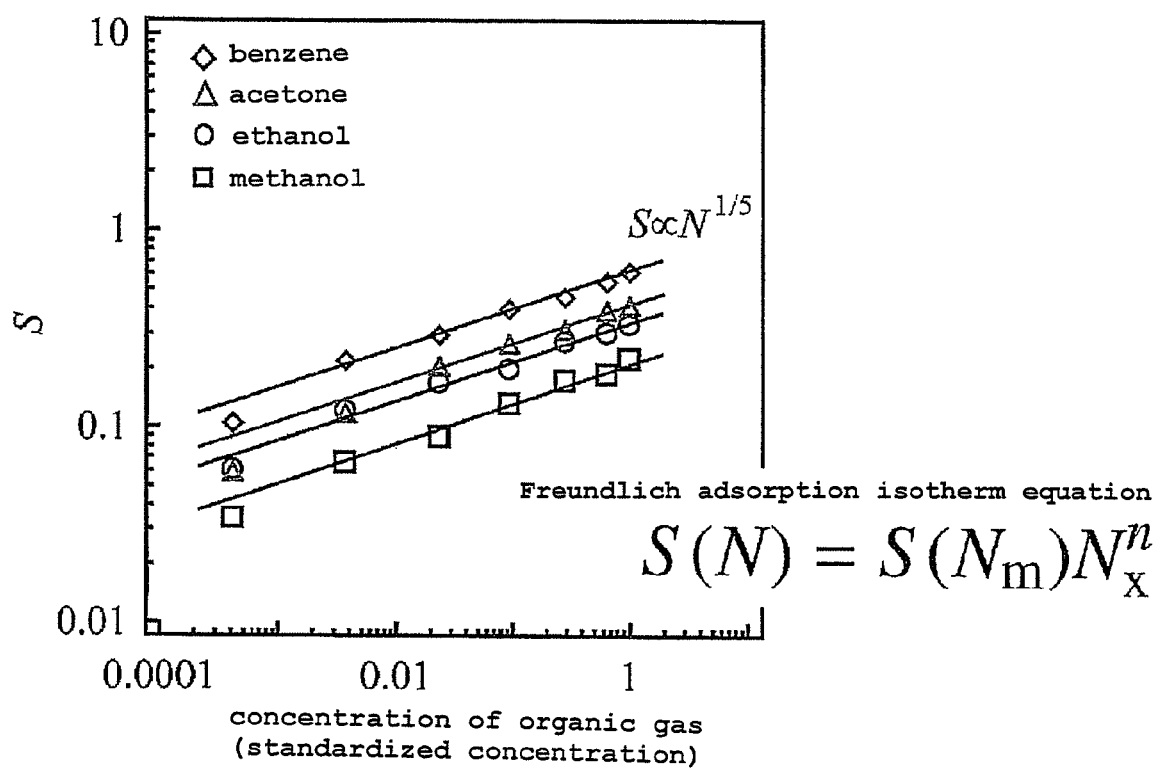
FIG. 15 shows organic gas concentration dependency of the gas sensor sensitivity ($S=\Delta I/I_0$) of the present invention.

FIG. 15 shows the relationship between the gas concentration (standardized data) of each of ethanol gas, methanol gas, acetone gas and benzene gas, and sensor sensitivity (S).

FIG. 15 shows a good match with the Freundlich adsorption isotherm equation. When the value was n=⅕, a good match was shown.

Therefore, when the kind of the organic gas is known, with the relationship between the concentration of such organic gas and the rate of current change ($\Delta I/I_0$) as the standard data, the concentration of a particular organic gas in the environment can be known.

INDUSTRIAL APPLICABILITY

Since the microcrystalline selenium of the present invention has high gas sensitivity, it can be used as a gas sensor. In addition, since the microcrystalline selenium of the present invention shows high adsorption capability of various organic gases, it can be used as an adsorbent of noxious gases.

EXPLANATION OF SYMBOLS 1 microcrystalline selenium
2 gas detector part
3 electrode
3A substrate electrode (copper plate)
3B gold thin film
4 electrode
4A substrate electrode (copper plate)
4B carbon tape
5 power source
6 variable resistance
7 voltmeter
8 amperometer
9A base
9B base
30 current value measurement part
100 gas sensor The present invention is based on patent application No. 2009-254461 filed in Japan, the contents of which are encompassed in full herein.

The invention claimed is:

1. A gas sensor having a device structure wherein an aggregate of selenium nanowires comprising hexagonal microcrystalline selenium is disposed between two electrodes and the aggregate of selenium nanowires forms a conducting path between the two electrodes,
wherein
the selenium nanowires overlap one another, and a clearance exists between adjacent selenium nanowires.

2. The gas sensor according to claim 1 which is for detection of an organic gas.

3. The gas sensor according to claim 2, wherein the organic gas is a gas derived from a volatile organic compound having a relative permittivity of 1.0-38.0 at room temperature.

4. The gas sensor according to claim 3, which identifies gaseous species from a difference in the magnitude of change in a value of an electric current flowing between two electrodes at a fixed voltage.

5. The gas sensor according to claim 3, which identifies, at a saturation sensitivity, gaseous species from a difference in the magnitude of change in a value of an electric current flowing between two electrodes.

6. The gas sensor according to claim 3, which identifies gaseous species from the difference in the temporal characteristic of the magnitude of change of a value of an electric current flowing between two electrodes at a fixed voltage, using difference in a relaxation time as an index.

7. The gas sensor according to claim 2, which identifies gaseous species from a difference in the magnitude of change in a value of an electric current flowing between two electrodes at a fixed voltage.

8. The gas sensor according to claim 2, which identifies, at a saturation sensitivity, gaseous species from a difference in the magnitude of change in a value of an electric current flowing between two electrodes.

9. The gas sensor according to claim 2, which identifies gaseous species from the difference in the temporal characteristic of the magnitude of change of a value of an electric current flowing between two electrodes at a fixed voltage, using difference in a relaxation time as an index.

10. The gas sensor according to claim 1, which identifies gaseous species from a difference in the magnitude of change in a value of an electric current flowing between two electrodes at a fixed voltage.

11. The gas sensor according to claim 1, which identifies, at a saturation sensitivity, gaseous species from a difference in the magnitude of change in a value of an electric current flowing between two electrodes.

12. The gas sensor according to claim 1, which identifies gaseous species from the difference in the temporal characteristic of the magnitude of change of a value of an electric current flowing between two electrodes at a fixed voltage, using difference in a relaxation time as an index.

13. The gas sensor according to claim 1, wherein the hexagonal microcrystalline selenium has a thickness that is not less than several nm and not more than 500 nm.

14. The gas sensor according to claim 1, wherein the hexagonal microcrystalline selenium has an aspect ratio L/D, wherein L represents length of the hexagonal microcrystalline selenium, and D represents thickness of, of not less than 5 and not more than 50.

15. The gas sensor according to claim 1, wherein the hexagonal microcrystalline selenium is fixed to a carbon tape fixed to one electrode of the two electrodes, and wherein the carbon tape is a two-faced adhesive tape containing a carbon powder as a conductive filler.

16. The gas sensor according to claim 15, wherein the other electrode of the two electrodes is a gold thin film.

17. The gas sensor according to claim 1, wherein the selenium nanowires have a random orientation.

* * * * *